US010765502B2

(12) United States Patent
Kassab

(10) Patent No.: US 10,765,502 B2
(45) Date of Patent: Sep. 8, 2020

(54) BLOOD FILTER DEVICES, SYSTEMS, AND METHODS OF USING THE SAME TO DETECT THE PRESENCE OF A THROMBUS WITHIN SAID FILTER DEVICES

(71) Applicant: 3DT Holdings, LLC, San Diego, CA (US)

(72) Inventor: Ghassan S. Kassab, La Jolla, CA (US)

(73) Assignee: 3DT Holdings, LLC, San Diego, CA (US)

( * ) Notice: Subject to any disclaimer, the term of this patent is extended or adjusted under 35 U.S.C. 154(b) by 276 days.

(21) Appl. No.: 15/724,216

(22) Filed: Oct. 3, 2017

(65) Prior Publication Data

US 2018/0092728 A1 Apr. 5, 2018

Related U.S. Application Data

(60) Provisional application No. 62/403,264, filed on Oct. 3, 2016.

(51) Int. Cl.
*A61F 2/01* (2006.01)
*A61B 5/053* (2006.01)
(Continued)

(52) U.S. Cl.
CPC .............. *A61F 2/01* (2013.01); *A61B 5/0084* (2013.01); *A61B 5/02007* (2013.01); *A61B 5/0215* (2013.01); *A61B 5/02158* (2013.01); *A61B 5/0538* (2013.01); *A61B 5/4851* (2013.01); *A61B 5/686* (2013.01); *A61B 5/6876* (2013.01);
(Continued)

(58) Field of Classification Search
CPC . A61B 5/0084; A61B 5/02007; A61B 5/0215; A61B 5/02158; A61B 5/0538; A61B 5/4851; A61B 5/686; A61B 5/6876; A61F 2/007; A61F 2/01; A61F 2002/0091; A61F 2002/011; A61F 2002/016; A61F 2220/0016; A61F 2250/0002
See application file for complete search history.

(56) References Cited

U.S. PATENT DOCUMENTS

2003/0083692 A1* 5/2003 Vrba ....................... A61F 2/013
606/200
2004/0230131 A1* 11/2004 Kassab .................. A61B 5/053
600/547

(Continued)

FOREIGN PATENT DOCUMENTS

JP 1221155 9/1989

*Primary Examiner* — Jocelin C Tanner
(74) *Attorney, Agent, or Firm* — Reichel Stohry Dean LLP; Mark C. Reichel; Natalie J. Dean

(57) ABSTRACT

Blood filter devices, systems, and methods of using the same to detect the presence of a thrombus within said filter devices. A device of the present disclosure for detecting a thrombus or other blood particulate matter of a threshold size within a vessel can comprise a filter having a head and a plurality of legs extending distally therefrom, configured to capture the thrombus or other blood particulate matter of at least a threshold size, and at least one impedance element positioned distal to the head and configured to detect a presence of the thrombus or other blood particulate matter of at least a threshold size within the filter by obtaining data within a bloodstream when the filter is positioned within the bloodstream.

18 Claims, 13 Drawing Sheets

(51) Int. Cl.
  *A61B 5/00*    (2006.01)
  *A61F 2/00*    (2006.01)
  *A61B 5/0215*  (2006.01)
  *A61B 5/02*    (2006.01)

(52) U.S. Cl.
  CPC .... *A61F 2/0077* (2013.01); *A61F 2002/0091* (2015.04); *A61F 2002/011* (2013.01); *A61F 2002/016* (2013.01); *A61F 2220/0016* (2013.01); *A61F 2250/0002* (2013.01)

(56) References Cited

U.S. PATENT DOCUMENTS

| | | | |
|---|---|---|---|
| 2005/0159791 A1* | 7/2005 | Daly | H04R 25/606 607/57 |
| 2006/0178695 A1* | 8/2006 | Decant, Jr. | A61B 5/02007 606/200 |
| 2006/0184193 A1* | 8/2006 | Lowe | A61F 2/01 606/200 |
| 2010/0106182 A1* | 4/2010 | Patel | A61F 2/013 606/200 |
| 2011/0125091 A1* | 5/2011 | Abbate | A61F 2/186 604/96.01 |
| 2012/0310269 A1* | 12/2012 | Fearnot | A61L 31/005 606/191 |
| 2014/0214149 A1* | 7/2014 | Kuraguntla | A61F 2/852 623/1.15 |
| 2014/0330143 A1* | 11/2014 | Kroh | A61B 5/0215 600/486 |
| 2015/0272449 A1* | 10/2015 | Meyer | A61B 5/0215 600/424 |
| 2016/0067449 A1* | 3/2016 | Misener | A61B 5/6852 600/409 |

\* cited by examiner (PRIOR ART)

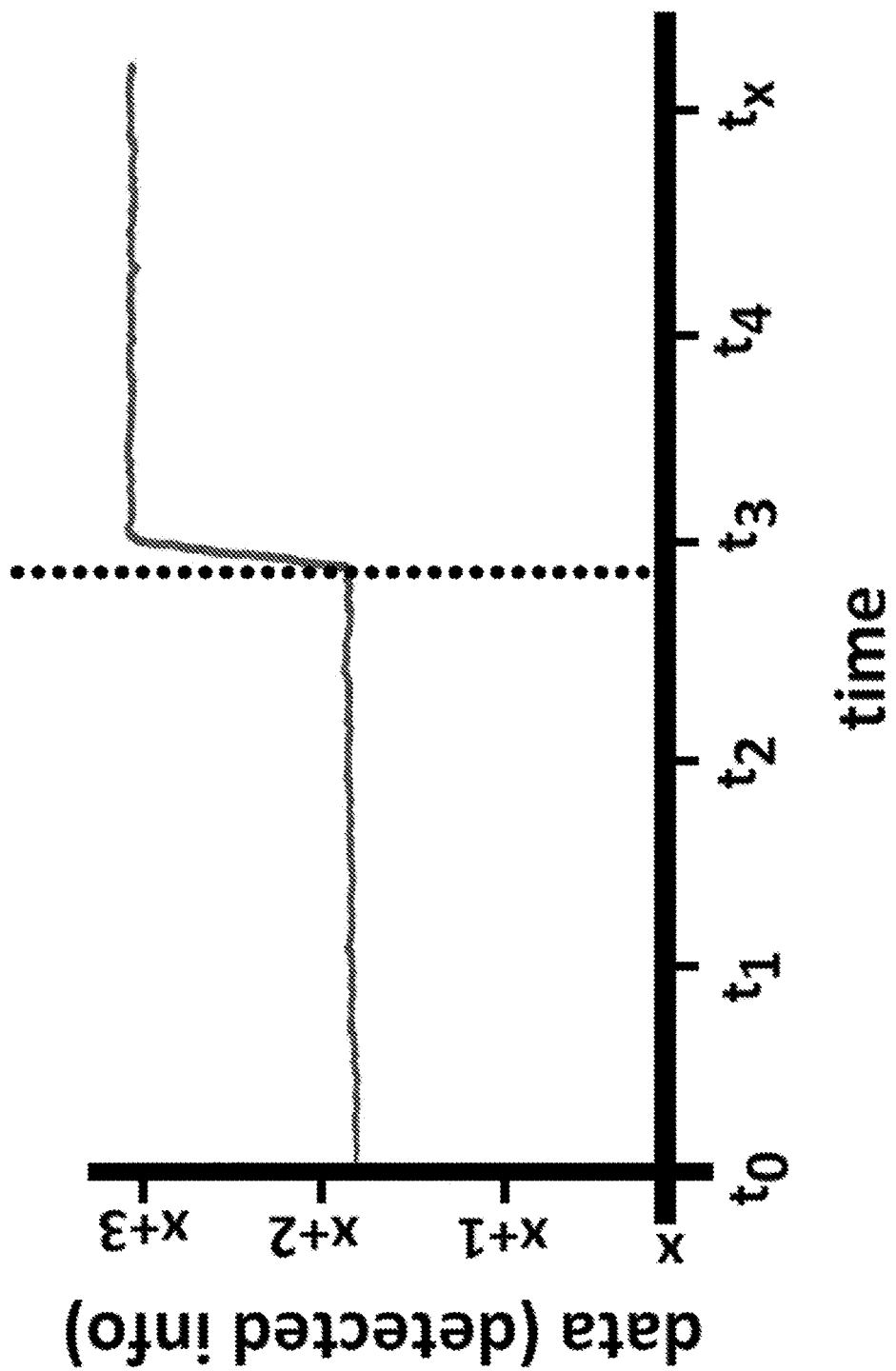

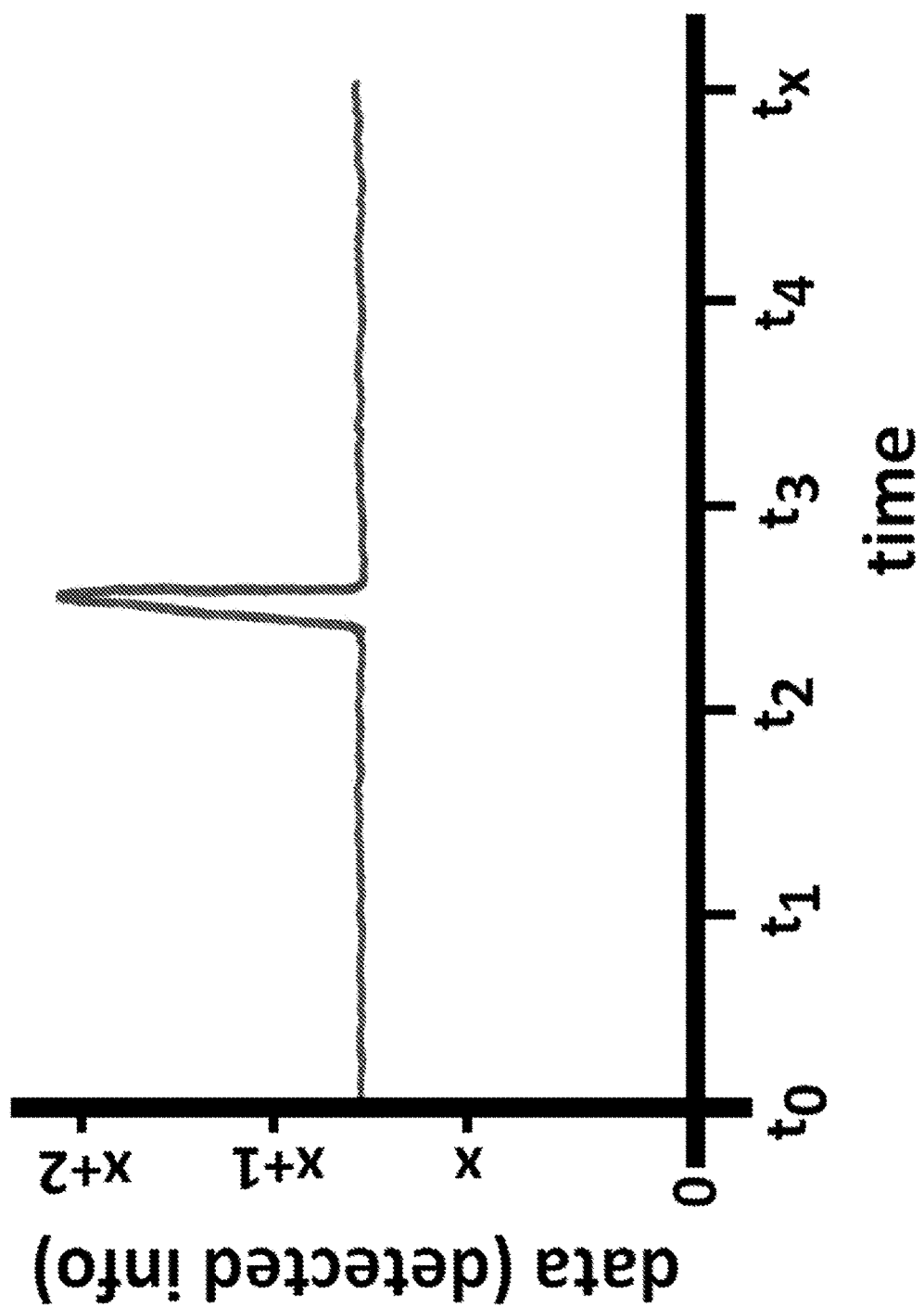

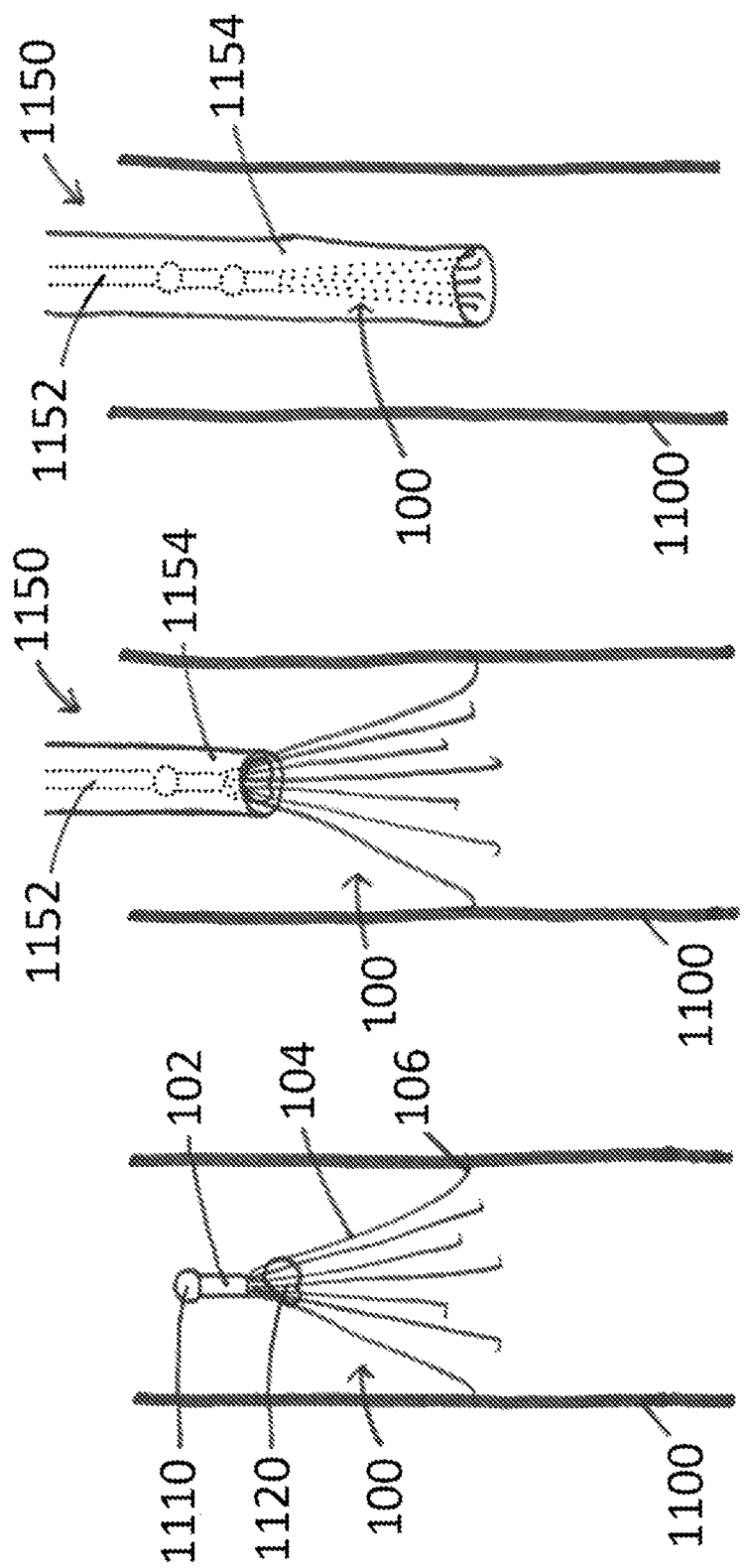

BLOOD FILTER DEVICES, SYSTEMS, AND METHODS OF USING THE SAME TO DETECT THE PRESENCE OF A THROMBUS WITHIN SAID FILTER DEVICES

PRIORITY

The present application is related to, and claims the priority benefit of, U.S. Provisional Patent Application Ser. No. 62/403,264, filed Oct. 3, 2016, the contents of which are incorporated herein directly and by reference in their entirety.

BACKGROUND

Vena cava filters are commonly used in the medical field to attempt to trap venous thrombi and to prevent them from entering and embolizing in the lungs. In an ideal situation, the vena cava filter would only be used as long as necessary, namely only as long as it would take to trap the one or more thrombi of particular and potential concern.

In view of the foregoing, it would be advantageous to have a mechanism to noninvasively detect a thrombus, or other blood particulate matter of a sufficient size, within a vena cava filter so to potentially minimize the implantation period.

BRIEF SUMMARY

The present disclosure includes disclosure of a device, comprising a filter comprising a head and a plurality of legs extending therefrom, configured to capture a thrombus or other blood particulate matter of at least a threshold size, and at least one additional item configured to detect a presence of the thrombus or other blood particulate matter of at least a threshold size within the filter by obtaining data within a bloodstream when the filter is positioned within the bloodstream.

The present disclosure includes disclosure of a device, wherein the at least one additional item comprises at least one impedance element, wherein the data comprises impedance data, wherein the at least one impedance element is configured to obtain the impedance data within a blood stream, and wherein the impedance data would indicate the presence of the thrombus or other blood particulate matter of at least a threshold size within the filter.

The present disclosure includes disclosure of a device, wherein the at least one additional item comprises at least one pressure sensor, wherein the data comprises pressure data, wherein the at least one pressure sensor is configured to obtain the pressure data within a blood stream, and wherein the pressure data would indicate the presence of the thrombus or other blood particulate matter of at least a threshold size within the filter.

The present disclosure includes disclosure of a device, wherein the at least one additional item comprises at least one fiber-optic sensor, wherein the data comprises light data, wherein the at least one fiber-optic sure sensor is configured to obtain light data within a blood stream, and wherein the light data would indicate the presence of the thrombus or other blood particulate matter of at least a threshold size within the filter.

The present disclosure includes disclosure of a device, wherein the device is at least partially coated with a coating comprising a fibroblast growth factor inhibitor.

The present disclosure includes disclosure of a system, comprising a device, comprising a filter comprising a head and a plurality of legs extending therefrom, configured to capture a thrombus or other blood particulate matter of at least a threshold size, and at least one additional item configured to detect a presence of the thrombus or other blood particulate matter of at least a threshold size within the filter by obtaining data within a bloodstream when the filter is positioned within the bloodstream; and a console configured to wirelessly obtain the data from the filter.

The present disclosure includes disclosure of a system, wherein the console is configured to obtain the data from the filter indicative of the thrombus or other blood particulate matter of at least a threshold size being caught within the filter.

The present disclosure includes disclosure of a system, wherein data can be transmitted from the device to the console and from the console to the device.

The present disclosure includes disclosure of a system, comprising a device, comprising a filter comprising a head and a plurality of legs extending therefrom, configured to capture a thrombus or other blood particulate matter of at least a threshold size, and at least one additional item configured to detect a presence of the thrombus or other blood particulate matter of at least a threshold size within the filter by obtaining data within a bloodstream when the filter is positioned within the bloodstream; and a sheath having a distal balloon positioned thereon, the sheath configured to be positioned around at least part of the filter within a blood vessel, wherein the balloon is configured for inflation within the blood vessel, wherein the inflation causes the balloon to inflate outward toward the blood vessel and proximally along the sheath.

The present disclosure includes disclosure of a device for detecting a thrombus or other blood particulate matter of a threshold size within a vessel, comprising a filter having a head and a plurality of legs extending distally therefrom, configured to capture the thrombus or other blood particulate matter of at least a threshold size; and at least one impedance element positioned distal to the head and configured to detect a presence of the thrombus or other blood particulate matter of at least a threshold size within the filter by obtaining data within a bloodstream when the filter is positioned within the bloodstream.

The present disclosure includes disclosure of a device, wherein the at least one impedance element comprises an excitation electrode configured to generate an electric field within the bloodstream when the filter is positioned within the bloodstream of a vessel. The present disclosure includes disclosure of a device, wherein the at least one impedance element comprises a detection electrode configured to detect conductance data within the bloodstream when the filter is positioned within the bloodstream of a vessel.

The present disclosure includes disclosure of a device, wherein the at least one impedance element comprises a combination excitation and detection electrode configured to both excite an electric field and detect conductance data within the electric field in the bloodstream when the filter is positioned within the bloodstream of a vessel. The present disclosure includes disclosure of a device, wherein the device further comprises at least one pressure sensor configured to obtain pressure data within a bloodstream, and wherein the pressure data indicates presence of the thrombus or other blood particulate matter of at least a threshold size within the filter.

The present disclosure includes disclosure of a device, wherein the device further comprises at least one fiber-optic sensor configured to obtain light data within a bloodstream, and wherein the light data indicates presence of the thrombus or other blood particulate matter of at least a threshold size within the filter. The present disclosure includes disclosure of a device, further comprising a sheath having a distal balloon positioned thereon, the sheath configured to be positioned around at least part of the filter within a blood vessel, wherein the balloon is configured for inflation within the blood vessel, wherein the inflation causes the balloon to inflate outward toward the blood vessel and proximally along the sheath.

The present disclosure includes disclosure of a device, wherein the device is at least partially coated with a coating comprising one or more fibroblast growth factor inhibitors. The present disclosure includes disclosure of a device, wherein the legs form a generally conical configuration and further comprise barbs on the distal ends thereof, the barbs configured for detachable engagement with vessel walls to hold the filter in place within the bloodstream of the vessel.

The present disclosure includes disclosure of a system for detecting a thrombus or other blood particulate matter of a threshold size within a vessel, comprising a device, comprising a filter having a head and a plurality of legs extending distally therefrom, configured to capture the thrombus or other blood particulate matter of at least a threshold size; and at least one impedance element positioned distal to the head and configured to detect a presence of the thrombus or other blood particulate matter of at least a threshold size within the filter by obtaining data within a bloodstream when the filter is positioned within the bloodstream; and a console operably coupled to the device, configured to wirelessly obtain data from the device, based the data received from the at least one impedance element positioned within the bloodstream of a vessel.

The present disclosure includes disclosure of a system, wherein the system further comprises a sheath having a distal balloon positioned thereon, the sheath configured to be positioned around at least part of the filter within a blood vessel, wherein the balloon is configured for inflation within the blood vessel, wherein the inflation causes the balloon to inflate outward toward the blood vessel and proximally along the sheath.

The present disclosure includes disclosure of a system, wherein the device may further comprise a filter transmitter/receiver, and wherein the console may further comprise a console transmitter/receiver, the filter transmitter/receiver operably coupled to the console transmitter/receiver to both transmit and receive the data detected by the at least one impedance element to and from the console.

The present disclosure includes disclosure of a system, wherein the filter transmitter/receiver and the console transmitter/receiver are operably coupled via a bidirectional radio frequency link.

The present disclosure includes disclosure of a system, further comprising a display operably coupled to the console, the display configured to visually or audibly provide the data received from the at least one impedance element positioned within the bloodstream of a vessel.

The present disclosure includes disclosure of a system, further comprising a remote computer operably coupled to the console, wherein the remote computer, the console, and the device can communicate with one another through a wireless network.

The present disclosure includes disclosure of a system, wherein the device is at least partially coated with a coating comprising a fibroblast growth factor inhibitor.

The present disclosure includes disclosure of a system, wherein the at least one impedance element comprises a combination excitation and detection electrode configured to both excite an electric field and detect conductance data within the electric field in the bloodstream when the filter is positioned within the bloodstream of a vessel.

The present disclosure includes disclosure of a system, wherein the device further comprises at least one sensor configured to obtain data within a bloodstream, and wherein the sensor data indicates presence of the thrombus or other blood particulate matter of at least a threshold size within the filter.

The present disclosure includes disclosure of a method for safely removing a blood filter device from within a blood vessel, comprising the steps of surrounding at least part of the blood filter device with a sheath retrieval device, the blood filter device configured to capture a thrombus or other blood particulate matter of at least a threshold size, the blood filter device comprising a head and a plurality of legs extending therefrom, and at least one impedance element positioned distal to the head and configured to detect a presence of the thrombus or other blood particulate matter of at least a threshold size within the blood filter device by obtaining data within a bloodstream when the blood filter device is positioned within the bloodstream; and inflating a balloon positioned on a distal end of the sheath retrieval device, wherein inflating the balloon within the blood vessel causes the balloon to inflate outwardly toward the blood vessel and proximally along the sheath, wherein the balloon at least partially surrounds the blood filter device; and retracting the blood filter device up into the sheath retrieval device while the balloon provides continuous pressure against the blood vessel walls to safely detach the legs of the blood filter device from the blood vessel walls of a patient.

The present disclosure includes disclosure of a method, wherein the step of surrounding at least part of the blood filter device further comprises inserting a catheter having a sheath retrieval device into the blood vessel of the patient.

The present disclosure includes disclosure of a system for detecting a thrombus or other blood particulate matter within a vessel, comprising a device, comprising a filter comprising a head and a plurality of legs extending therefrom, configured to capture a thrombus or other blood particulate matter of at least a threshold size, and at least one additional item configured to detect a presence of the thrombus or other blood particulate matter of at least a threshold size within the filter by obtaining data within a bloodstream when the filter is positioned within the bloodstream; and a sheath having a distal balloon positioned thereon, the sheath configured to be positioned around at least part of the filter within a blood vessel, wherein the balloon is configured for inflation within the blood vessel, wherein the inflation causes the balloon to inflate outward toward the blood vessel and proximally along the sheath.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIGS. 6A, 6B, and 7 show depictions of data collected over time, by way of example for discussion purposes, according to exemplary embodiments of the present disclosure;

FIG. 11A shows a filter positioned within a vein, according to an exemplary embodiment of the present disclosure;

FIG. 11B shows a sheath being advanced distally over a filter, according to an exemplary embodiment of the present disclosure;

FIG. 11C shows a filter fully encapsulated within a sheath and engaged using a retrieval device, according to an exemplary embodiment of the present disclosure;

Figure 1:
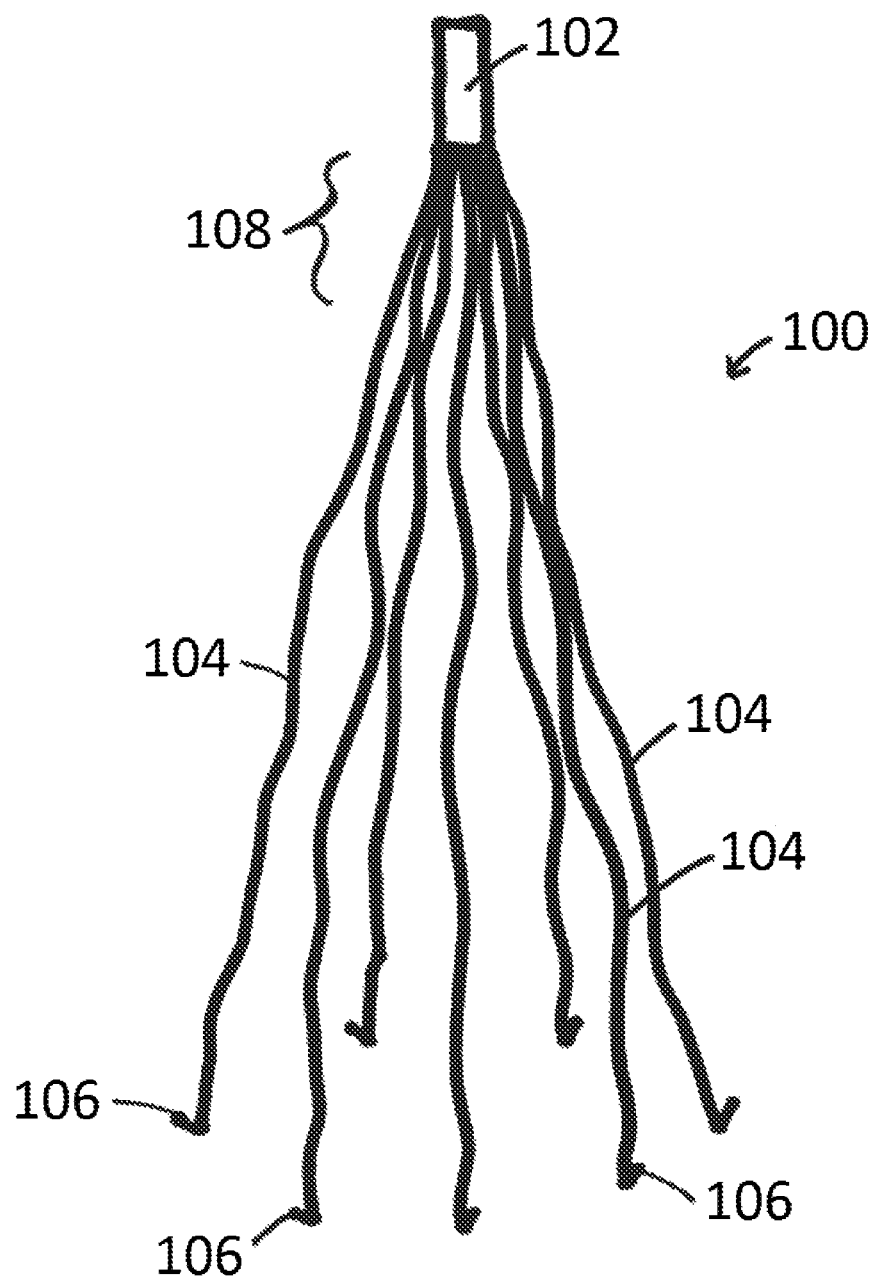
FIG. 1 shows a prior art vena cava filter.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 shows an embodiment of a prior-art vena cava filter. As shown therein, filter 100 comprises a head 102 having a plurality of legs 104 extending therefrom, whereby the plurality of legs 104 form a general conical configuration. Barbs 106 may optionally be present at distal ends of legs 104 so that when filter 100 is implanted within a vein or other vessel, for example, barbs 106 could gently engage venous tissue to hold filter 100 in place. Particulates within the blood stream of sufficient size so to be caught/trapped by filter 100, such as a blood clot (thrombus) or other blood particulate matter, such as cholesterol, plaque, etc., of sufficient size to be caught/trapped by filter 100, could then be caught/trapped by filter 100 at or near head 102 of filter 100, such as at or near apex 108 of filter 100, as shown in FIG. 1 (whereby apex 108 is defined as an area just distal to head 102 of filter 100, where legs 104 contact head 102, and being the location where a thrombus or other blood particulate matter would ultimately be caught by filter 100).

It is noted that in various filter 100 devices of the present disclosure, a head 102 may not be a separate element from legs 104. For example, a location where legs 104 meet at a location of filter 100 may be referred to as head 102.

Figure 2:
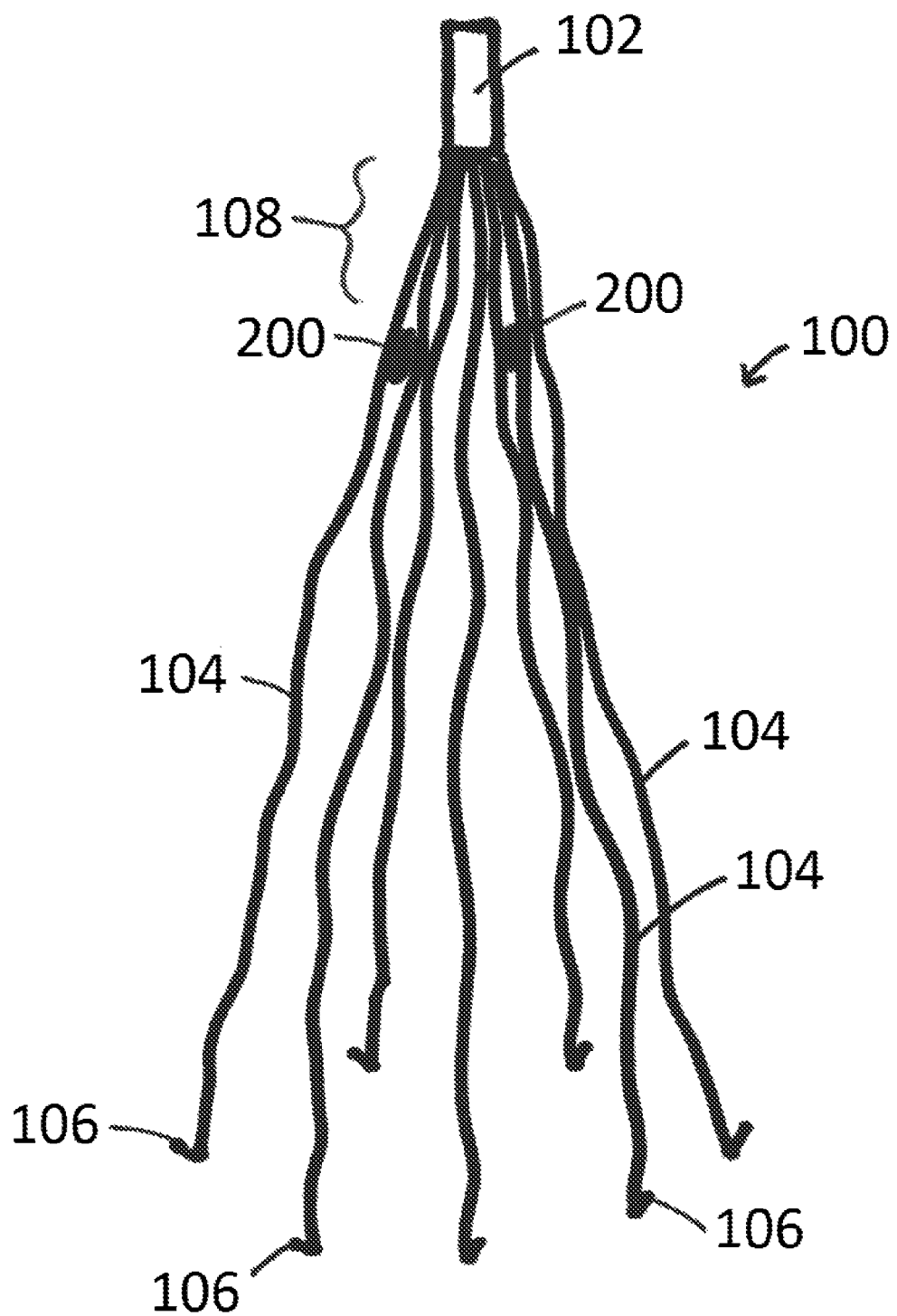
FIG. 2 shows a filter having impedance elements coupled thereto at one or more legs, according to an exemplary embodiment of the present disclosure.

An exemplary filter 100 of the present disclosure is shown in FIG. 2. As shown in FIG. 2, filter 100 is a "smart" filter in that it contains components, or is otherwise configured, to allow a medical professional, for example, to noninvasively determine whether or not a thrombus or other blood particulate matter is present within (caught/trapped by) said filter 100 after implantation into the bloodstream.

As shown in FIG. 2, an exemplary filter 100 of the present disclosure comprises one or more impedance elements 200 positioned upon or otherwise configured as part of filter. For example, impedance elements 200 could comprise metallic elements or impedance electrodes that are configured as part of an overall system to determine impedance. The impedance of blood, or a general impedance range of blood, differs from the impedance of a blood clot (thrombus), or an impedance range of thrombi. As such, changes in impedance can indicate the presence of a thrombus, or other blood particulate matter of a sufficient size so to be caught by filter 100, within filter 100, as referenced in further detail herein.

Such a method to determine the presence of a thrombus or other blood particulate matter of s sufficient size to be caught by filter 100 within filter 100 would therefore be based upon a detected change in impedance. For example, and after implantation of filter 100, impedance data could be obtained from filter 100 over time or otherwise as desired. For example, and should a thrombus not be caught by filter 100 until five days after implantation has elapsed, said impedance data would be relatively steady over those initial five days, and then a notable change in impedance would be detected, indicative of the capturing of said thrombus.

Impedance elements 200 may be excitation electrodes, detection electrodes, or combination excitation/detection electrodes. Excitation electrodes (exemplary impedance elements 200) can be used to generate an electric field, and detection electrodes (also exemplary impedance elements 200) can detect, using impedance (or conductance, depending on the preference in terminology), within said electric field. For example, if a combination of excitation electrodes and detection electrodes (exemplary impedance elements 200) were operated within the bloodstream, as generally referenced herein, constant or relatively constant impedance data would be obtained over time if only blood is present at said impedance elements 200. Should a thrombus or other blood particulate matter of s sufficient size to be caught by filter 100 be caught/captured by filter 100 and be within the electric field, said impedance elements 200 could then effectively detect the presence of said thrombus and/or other particulate matter, as a change in impedance would occur based on said presence, as compared to, for example, the lack thereof (only standard blood flow, as referenced above). Said details on use of excitation electrodes and/or detection electrodes (exemplary impedance elements 200) within the blood stream to obtain conductance/impedance data using impedance, for example, may be as described within U.S.

Pat. No. 7,454,244 to Kassab et al., the contents of which are incorporated into the present disclosure by reference in their entirety.

In various filter embodiments 100 of the present disclosure, filter 100 itself may be configured for use as an impedance element 200. In such an embodiment, filter 100 may operate as an impedance element 200, and one or more additional impedance elements 200 may be present upon said filter 100.

In various embodiments of filters 100 having impedance elements 200 of the present disclosure, the electric field can be generated by impedance elements 200 of the filter 100 or other impedance elements 200 positioned away from the filter 100 within or outside of the body, such as within another part of the body outside of the bloodstream or within the bloodstream away from filter 100, or outside of the body, such as on the skin, for example.

Figure 3:
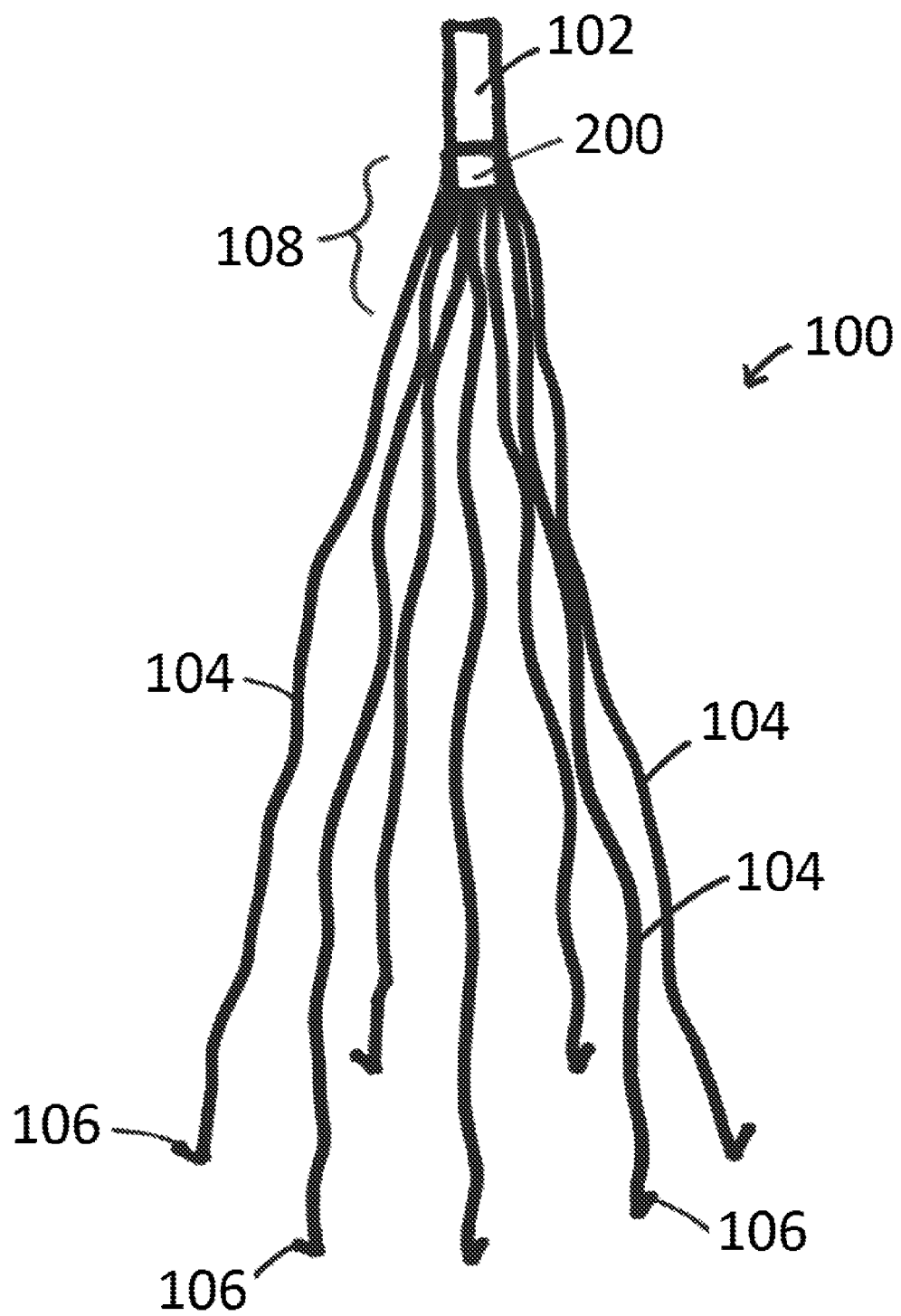
FIG. 3 shows a filter having impedance elements coupled thereto at a head of the filter, according to an exemplary embodiment of the present disclosure.

The one or more impedance elements 200 could be coupled to one or more legs 104 of filter 100 at or near head 102, such as shown in FIG. 2. Conversely, the one or more impedance elements 200 could be coupled to head 102 of filter 100, such as shown in FIG. 3. In various embodiments, one or more impedance elements 200 could be coupled to one or more legs 104 and/or to head 102 of filter 100.

Figure 4:
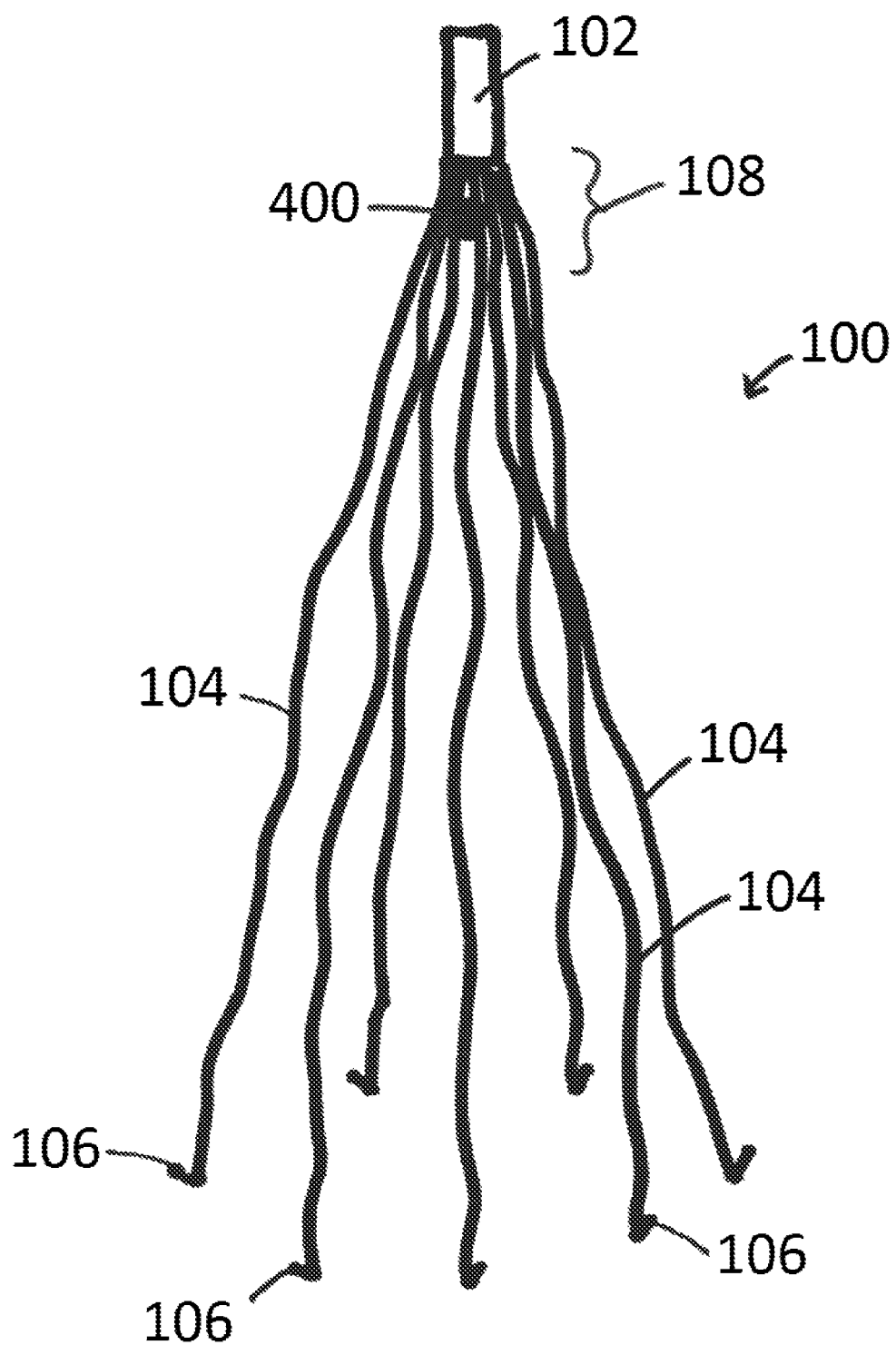
FIG. 4 shows a filter having one or more pressure sensors, according to an exemplary embodiment of the present disclosure.

FIG. 4 shows another embodiment of an exemplary filter 100 of the present disclosure. As shown in FIG. 4, filter 100 comprises one or more pressure sensors 400 configured to detect pressures (obtain pressure data) within a bloodstream of a patient. For example, and should pressure sensor be operated over time during typical blood flow (for a particular patient, for example), the pressure data obtained by pressure sensor(s) 400 would have a steady pulse form. Should a thrombus or other blood particulate matter of a sufficient size to be caught by filter 100 be caught/captured by filter 100 and contact one or more pressure sensors 400, the pressure data obtained by said pressure sensor(s) 400 would damp out the pulse form and become less pulsatile or even flat line indicative of a thrombus on the transducer tip. This dampening of pressure is well known when a clot forms around the tip of a catheter during pressure measurements that requires flushing to restore the pulsatility of the pressure waveform. Pressure sensors 400 of the present disclosure can be coupled to or otherwise integrated with one or more legs 104 of filter 100 and/or head 102 of filter 100, as may be desired.

Figure 5:
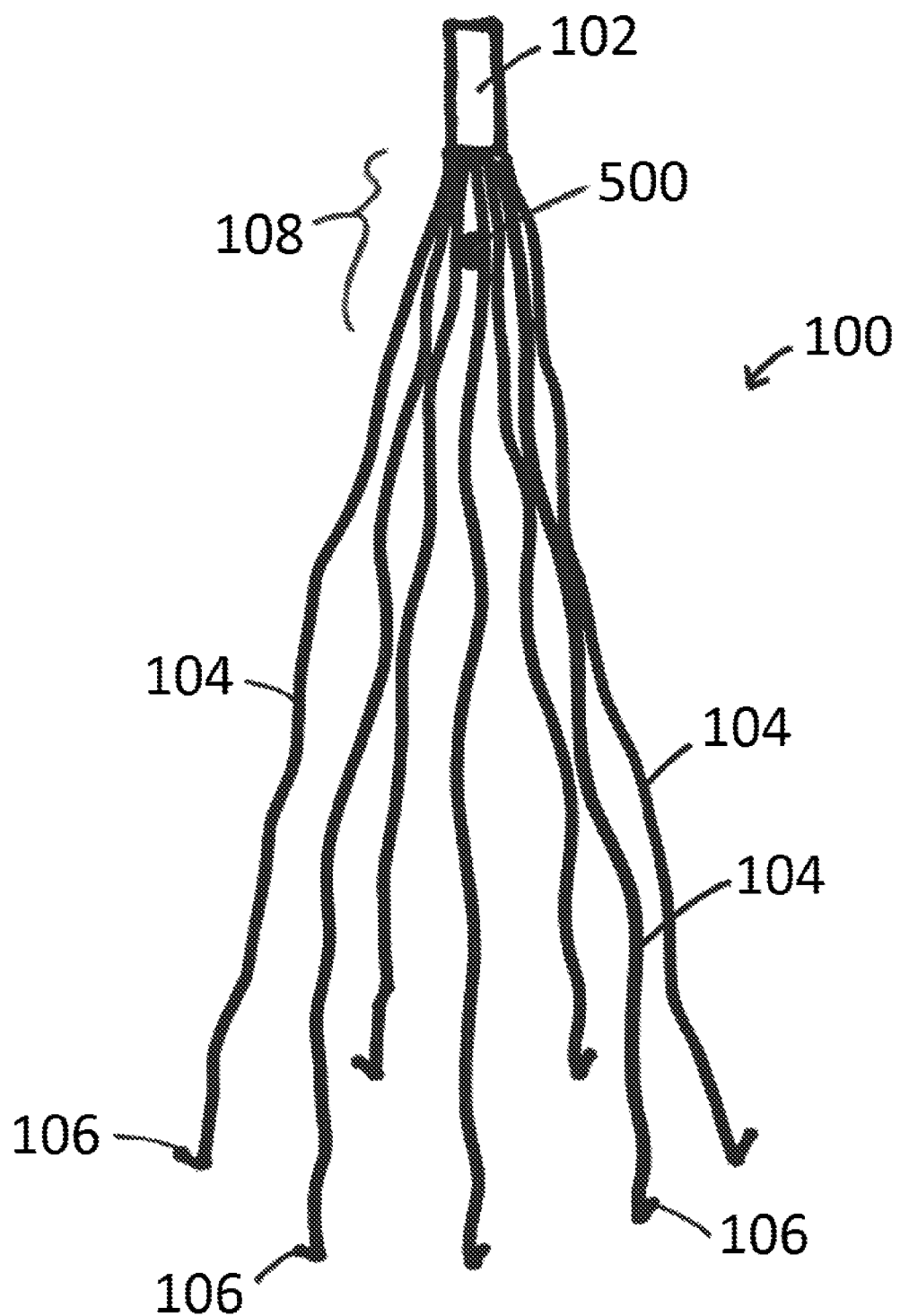
FIG. 5 shows a filter having one or more pressure sensors, according to an exemplary embodiment of the present disclosure.

FIG. 5 shows another embodiment of an exemplary filter 100 of the present disclosure. As shown in FIG. 5, filter 100 comprises one or more fiber-optic sensors 500 configured to detect a thrombus or other blood particulate matter using light. Fiber-optic sensors 500 can be coupled to filter 100 and when operated, are configured to detect blood particulate matter above a certain size threshold, such as larger than a red blood cell or a set number of red blood cells. Should a thrombus or other blood particulate matter of a sufficient size so to be caught by filter 100 be caught by filter 100 within a sensing range of one or more fiber-optic sensors 500, data obtained by said fiber-optic sensor(s) 500 would be different than data obtained by the same fiber-optic sensor(s) 500 when a thrombus or other blood particulate matter of a sufficient size so to be caught by filter 100 is absent from filter 100.

As referenced herein, impedance elements 200, pressure sensors 400, and/or fiber-optic sensors 500 can be positioned along filter 100 so that said items contact head 102 of filter 100 and/or contact one or more legs 104 of filter 100, as may be desired, at head 102, just distal to head 102 (such as at apex 108), or distal to apex 108.

Figure 6B:
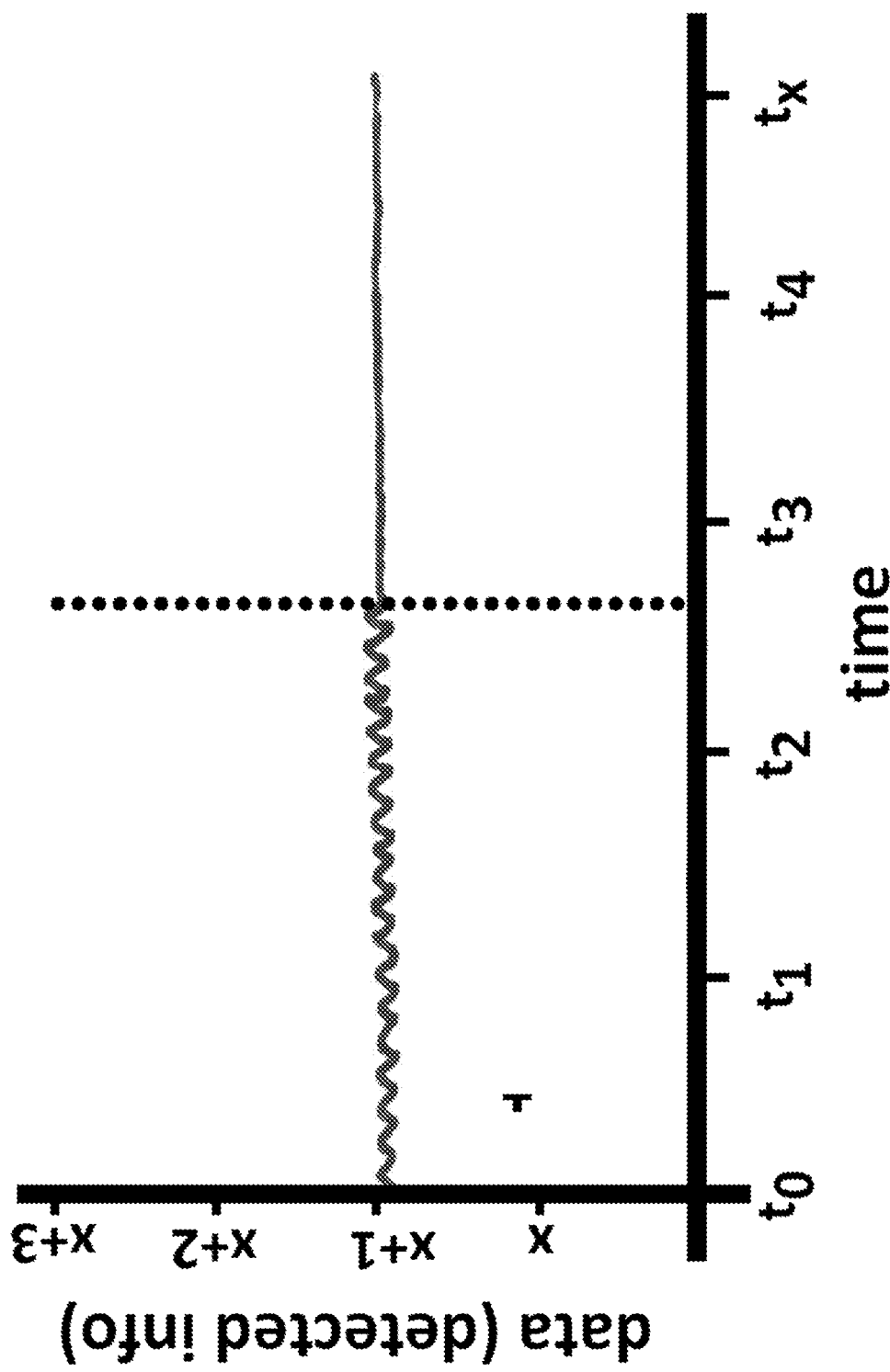

FIGS. 6A, 6B and 7 show depictions of data collected over time, by way of example for discussion purposes (as FIGS. 6 and 7 do not depict data actually collected). The data depiction in FIG. 6A would represent, for example, relatively constant data obtained over time, and a change in the intensity of said data upon and after a thrombus, or other blood particulate matter of a sufficient size so to be caught by filter 100, is caught by filter 100. For example, FIG. 6 could depict impedance data collected over time, such as by operating one or more impedance elements 200 of the present disclosure, with a notable change in impedance upon capture of a thrombus by filter 100, as said thrombus would have different impedance properties as compared to blood. FIG. 6A could also depict light data collected over time, such as by operating one or more fiber-optic sensors 500 of the present disclosure, with a notable change in said light data upon capture of a thrombus by filter 100 when said thrombus is within a detection range of said fiber-optic sensors 500. FIG. 6B could represent, for example, a steady pulse form of pressure data obtained over time using one or more pressure sensors 200, which dampens, or even potentially flat lines, when a thrombus, or other or other blood particulate matter of a sufficient size so to be caught by filter 100, is caught by filter 100 and impedes the ability of pressure sensor(s) 200 to obtain pressure data.

The data depiction in FIG. 7 could represent, for example, a temporary change impedance, such as when a thrombus would be temporarily detected by impedance elements 200 positioned away from apex 108, for example, such that the thrombus would enter filter 100, pass through a detection range of impedance elements 200, and then be caught within apex 108 of filter. The data depiction in FIG. 7 could also represent, for example, a temporary change in pressure, such as when a thrombus would temporarily contact a pressure sensor 400 positioned away from apex 108, for example, such that the thrombus would enter filter 100, briefly contact pressure sensor 400, and then be caught within apex 108 of filter. The data depiction in FIG. 7 could also represent, for example, a temporary change in light data obtained by fiber-optic sensors, such as when a thrombus would be temporarily detected using fiber-optic sensor(s) 500 positioned away from apex 108, for example, such that the thrombus would enter filter 100, briefly be detected by fiber-optic sensor(s) 500, and then be caught within apex 108 of filter.

Figure 8:
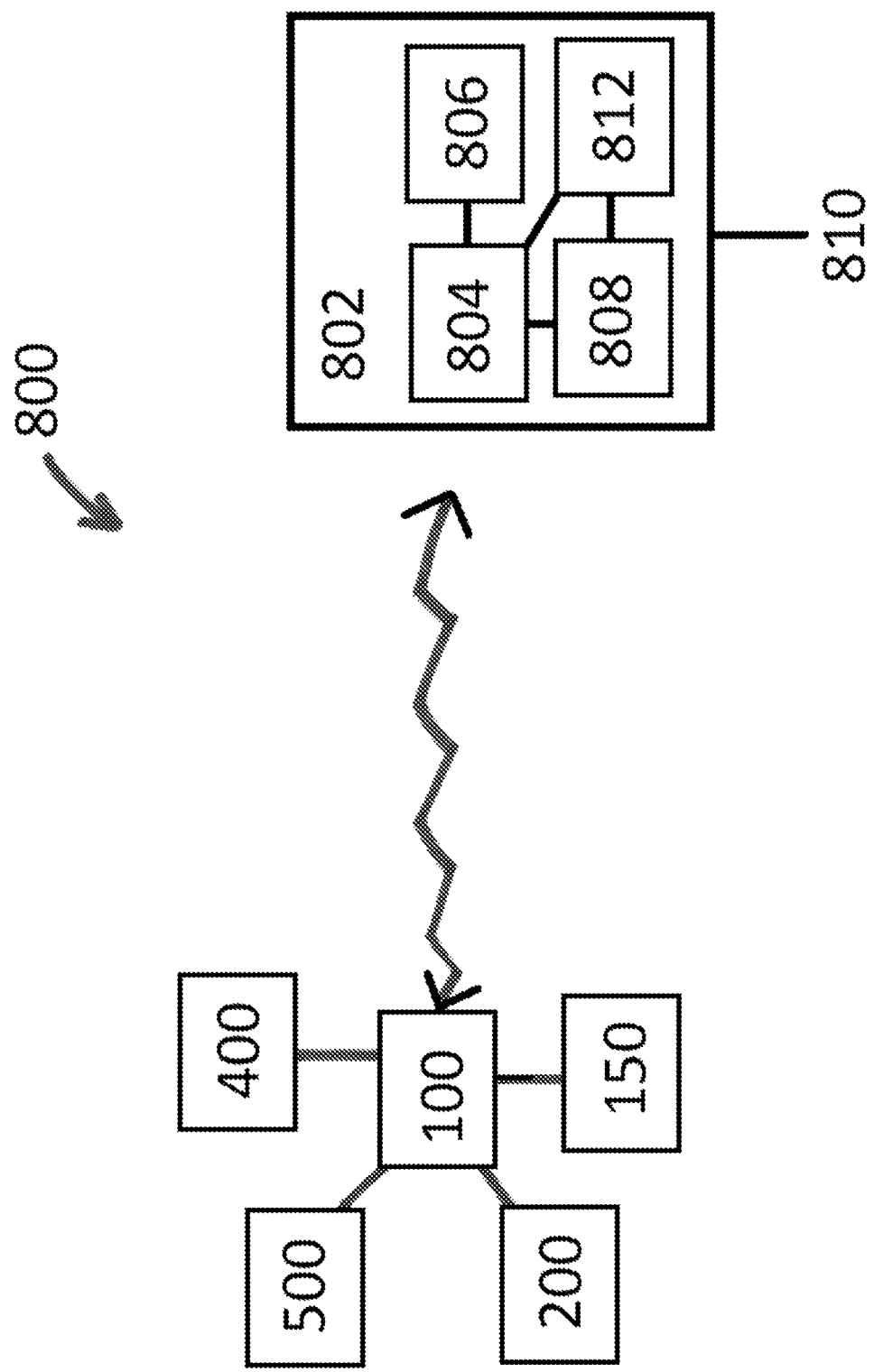
FIG. 8 shows a block component diagram of components of a system, according to an exemplary embodiment of the present disclosure.

FIG. 8 shows a block component diagram of an exemplary system 800 of the present disclosure. An exemplary system 800 of the present disclosure comprises a filter 100 having one or more impedance elements 200, pressure sensors 400, and/or fiber-optic sensors 500 positioned thereon and/or coupled thereto, and a console 802 (such as a computer or another piece of equipment having a processor 804 coupled to a storage medium 806, whereby the storage medium can store instructions (software) accessible using processor 804 to operate console 802 as desired). Console 802, in various embodiments, would be configured to obtain one or more of impedance data from impedance elements 200, pressure data from pressure sensors 400, and/or light data from fiber-optic sensors 500, of filter 100, when filter 100 is implanted within a mammalian body (such as within a mammalian vein). Said data (depicted as the jagged line in FIG. 8) can be obtained directly by said impedance elements 200, pressure sensors 400, and/or fiber-optic sensors 500, and/or by way of a filter transmitter/receiver 150 in communication therewith, such as also coupled to filter 100, whereby filter transmitter/receiver 150 is configured to transmit said data to console 802, such as being received by a console transmitter/receiver 808, for example. As data is obtained from filter 100 by console 802, said data can be stored within storage medium 806 (such as hard drive, flash drive, solid state drive, optical drive, etc.), be used by processor 804 as desired, and/or displayed using a display 810 coupled to or otherwise in communication with console 802. Display 810 can be a video display, an audio mechanism (such as a speaker), etc., namely some sort of item that could be operated to alert a user that the data has been received, and in particular, for example, alert a user that the data indicates that a thrombus, or other blood particulate matter of a sufficient size so to be caught by filter 100, is caught by/within filter 100. Once this has occurred, a medical professional may wish to remove, clean, and/or replace said filter 100, as may be desired. Should a particular goal be to limit the amount of time a filter 100 is present within a vein, such a filter 100 and/or system 800, as referenced herein, could be used and operated to detect a thrombus, or other blood particulate matter of a sufficient size so to be caught by filter 100, as soon as it is captured by filter 100, allowing said filter 100 to be removed with the knowledge that it has caught a thrombus/other matter, so to avoid potential complications and/or long-term implants.

An exemplary telemetry system (system 800), such as shown in FIG. 8, allows wireless excitation of the various sensors (such as impedance element(s) 200, pressure sensor(s) 400, and/or fiber-optic element(s) 500) and transmission of the data obtained from the same telemetrically. System 800 can include a bidirectional radio frequency link (such as depicted as the jagged line in FIG. 8, for example) that allows the implant (filter 100) to send data to console 802 and to accept commands/instructions from console 802, such as via software stored on storage medium 806) to perform various tasks. Said instructions can be received by filter transmitter/receiver 150, as shown in FIG. 8, which can also be used to transmit data back to console 802. System 800 can be controlled or otherwise operated by a base station decoder/controller 812, such as shown in FIG. 8 and in communication with console transmitter/receiver 808 and/or processor 804) that decodes the data stream sent by the implant (filter 100) into analog signals. System 800 can also convert the data into a digital data stream that can be sent via Ethernet, for example, to a remote computer or iPhone for storage and/or analysis.

Figure 9:
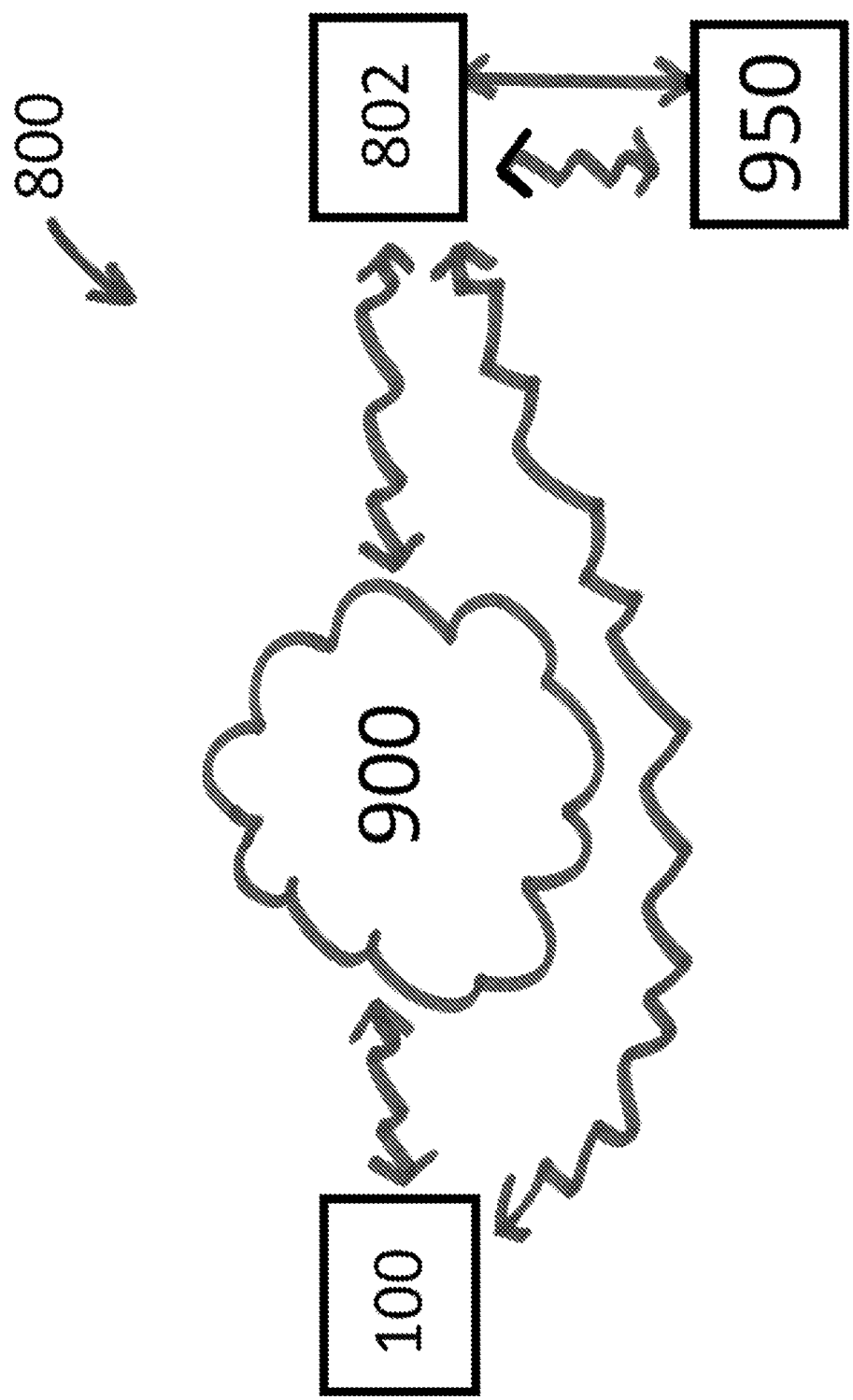
FIG. 9 shows components of a system communication with one another directly or through a network, according to an exemplary embodiment of the present disclosure.

FIG. 9 shows portions of an exemplary system 800, whereby console 802 and filter 100 can effectively communicate with one another directly or through a network 900. Data can be sent to console 802 from filter 100, from filter 100 to console 802, from console 802 to a remote computer 950 in wired or wireless communication with console 802, and/or to console 802 from remote computer 950 in wired or wireless communication with console 802, as may be desired. Remote computer 950 could be, for example, a laptop, tablet, smartphone (such as an iPhone or Android device), laptop, or even another console 802.

In use, when a filter (such as filter 100 or prior art filters) remain within a blood vessel for an extended period of time, such as more than several months, they tend to become encapsulated with fibrotic ingrowth, which can not only hinder blood flow, but can also make removal of said filter quite difficult. Depending on the extent of fibrotic ingrowth, removal of the filter may require a surgical procedure versus an intravascular procedure.

Figure 10:
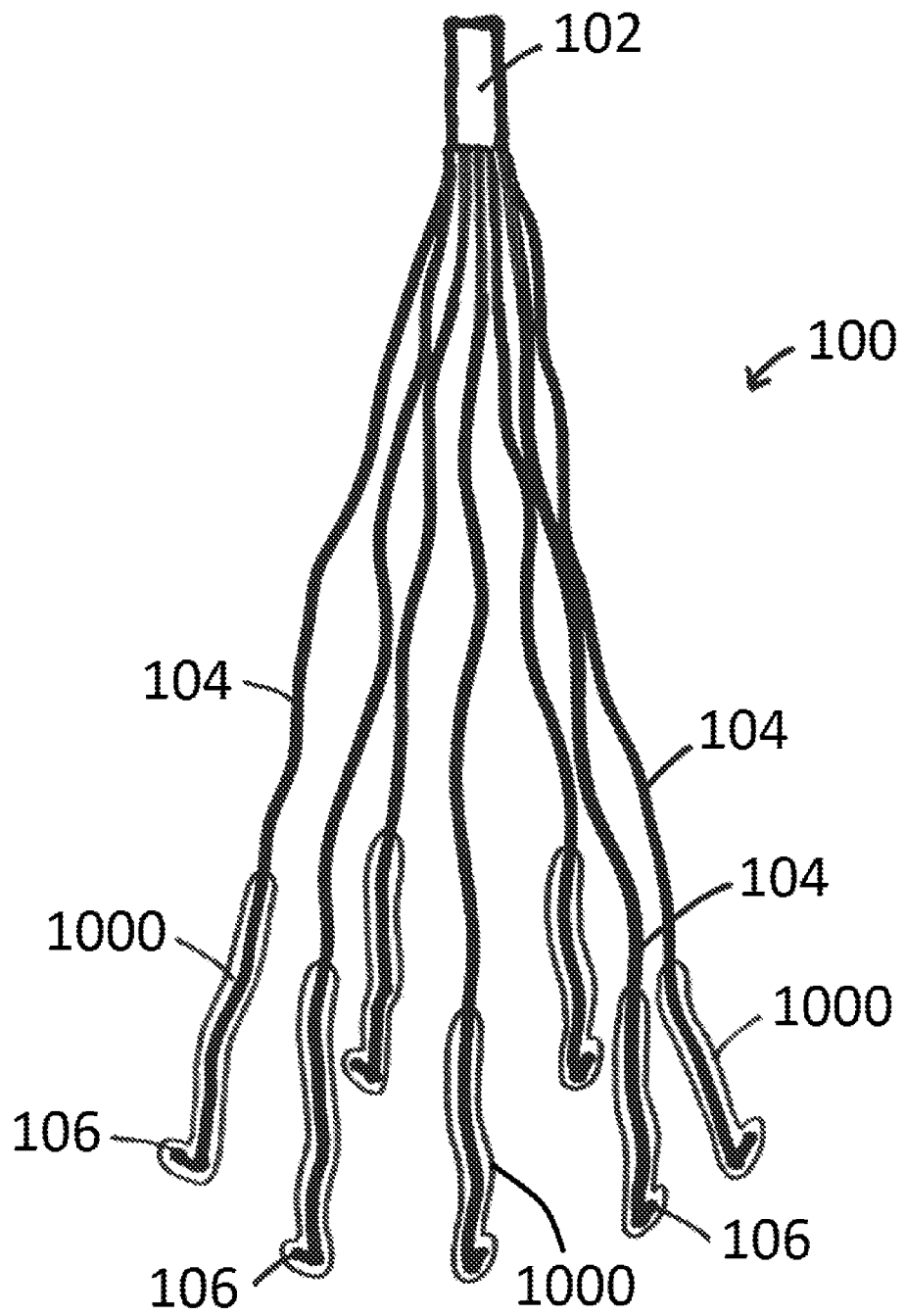
FIG. 10 shows a filter having a coating positioned thereon, according to an exemplary embodiment of the present disclosure.

To address potential fibrotic ingrowth and inhibit or limit the same, exemplary filters 100 of the present disclosure can be partially or completely coated with a coating 1000, such as shown in FIG. 10. Coatings 1000, in various embodiments, can comprise one or more fibroblast growth factor (FGF) inhibitors 1002 that can release said inhibitors over time. In at least one embodiment, at least portions of the arms 104 of an exemplary filter 100 that would ultimately contact a blood vessel (such as a vein) can be coated with coating 1000 so to release an FGF inhibitor 1002 over time. Exemplary FGF inhibitors 1002 (also referred to as fibrosis inhibitors) of the present disclosure may include, but are not limited to, Suramin (8,8'-{Carbonylbis[imino-3,1-phenylenecarbonylimino(4-methyl-3,1-phenylene)carbonylimino]}di(1,3,5-naphthalenetrisulfonic acid) or other polyanionic polysulfated or polysulfonated compounds such as suradistas (sulfonated distamycin A derivatives), for example.

In cases where a barbs 106 of legs 104 of filter 100 would penetrate and migrate into a vessel wall, a sheath used to retract the filter 100 can at times almost invert the inferior vena cavae (IVC) (an exemplary vein 1100) when filter 100 is pulled therethrough, as said barbs 106 coupled with the pulling can exert a relatively large force on a pliable venous wall. Procedurally, a filter (such as filter 100) would be positioned within a vein 1100, such as shown in FIG. 11A, and allowed to remain therein for a desired amount time so to capture a thrombus or other material 1120. To remove the filter (such as a filter 100), a retrieval system 1150 would be used, such as shown in FIG. 11B, with said system 1150 comprising a retrieval device 1152 positioned within a sheath 1154. Retrieval device 1152 would engage head 102 of filter 100, or an engagement portion 1110 at, near, or of head 102 of filter 100, and after said engagement, sheath 1154 could be advanced, or otherwise sheath 1154 would move relative to retrieval device 1152, so to encapsulate filter within sheath 1154, such as shown in FIG. 11C. Retrieval system 1150 can then be removed from vein 1100, taking filter 100 out of vein 1100 as well. As noted above, barbs 106 can engage vein 1100, or fibrotic tissue can engage legs 104 or barbs 106 of filter 100, and retrieving filter 100 such as shown in FIGS. 11B and 11C and referenced above, can cause undesired stress (force) against the wall of vein 1100, which can lead to potentially serious complications during removal.

To address this problem, a balloon 1200 on a distal external portion of sheath 1154 that can be inflated to apply tension to the IVC (vein 1100) wall during retraction, so to concentrate the force on the tips of the filter (barbs 106 of filter 100) where needed without unduly stretching the IVC wall. Current sheaths used to remove filters, such as shown in FIGS. 11B and 11C) do not use or include balloons 1200, and as such, sheaths 1154 of the present disclosure that incorporate balloons 1200 therein would be novel and would provide a novel "push and pull" anchor mechanism for easier filter 100 retrieval.

Figure 12C:
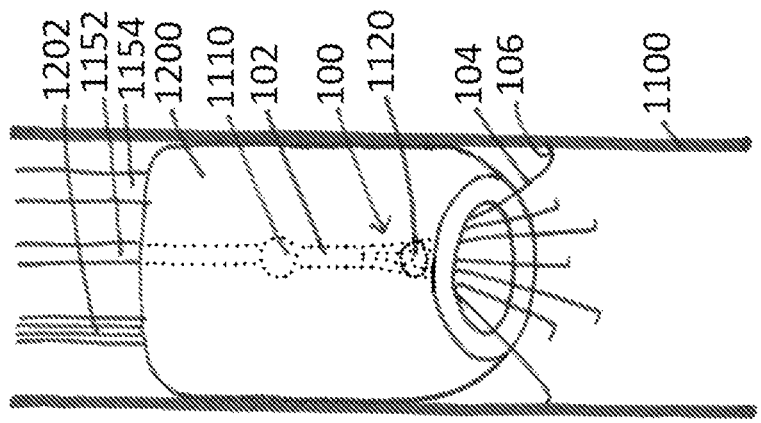
FIG. 12C shows full (or more) inflation of a balloon of a sheath within a vein, according to an exemplary embodiment of the present disclosure.
Figure 12B:
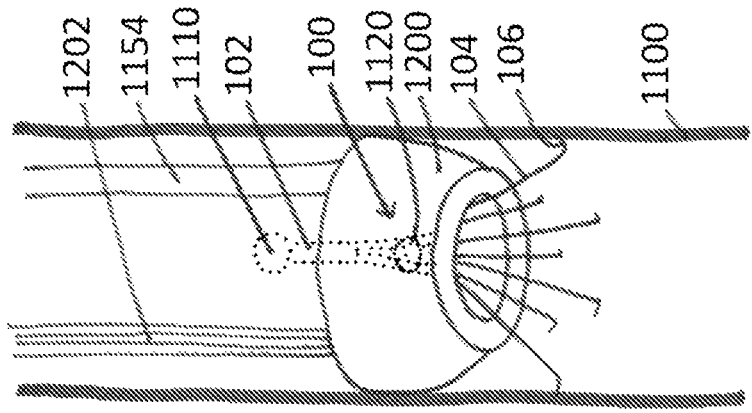
FIG. 12B shows partial inflation of a balloon of a sheath within a vein, according to an exemplary embodiment of the present disclosure.
Figure 12A:
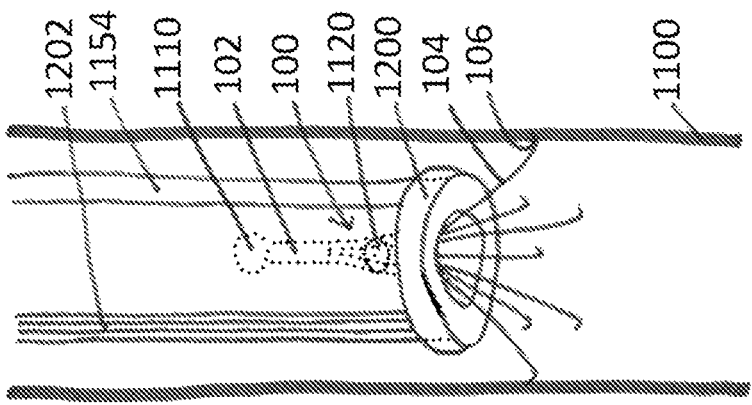
FIG. 12A shows a sheath advanced distally over some or most of a filter, according to an exemplary embodiment of the present disclosure.

FIG. 12A shows a sheath 1154 advanced within a vein 1100 so that sheath 1154 encapsulates some/most of filter 100. Barbs 106 of legs 104 of filter 100 generally would remain attached to vein 1100, although advancement of sheath 1154 around filter 100, such as shown in FIG. 12A, may cause one or more barbs 106 to detach. Once sheath 1154 is positioned as desired, a sheath balloon 1200 positioned at or near a distal end of sheath 1154 can be inflated, such as shown in FIG. 12B (partial inflation) and FIG. 12C (fully inflated or more inflated than in FIG. 12B), whereby balloon 1200 inflates outward toward vein 1100 and proximally along sheath 1154, such as shown in FIGS. 12B and 12C. In at least one embodiment, balloon 1200 is configured to extend at or about 10 cm, or more or less, along sheath 1154. Inflation of balloon 1200 can occur via an inflation lumen 1202, such as shown in FIGS. 12A-12C, defined within or outside of sheath 1154. Inflation of balloon 1200, such as shown in FIG. 12C, provides tension against vein 1100, so that when a retrieval device 1152 engages filter 100 to retrieve the same through sheath 1154, a much more focal application of force would be used to retract filter 100 and prevent vein 1100 from substantially deforming. For example, and as noted above, barbs 106 would pull vein 1100 inward, and if a balloon 1200 is used and inflated, balloon 1200 would counter that pulling and help vein 1100 remain in position while filter 100 is being removed from vein 1100.

The aforementioned filters 100, wireless systems 800, and sheaths 1154 would be well received in the medical marketplace.

While various embodiments of blood filter devices, systems, and methods of using the same to detect the presence of a thrombus within said filter devices have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device for detecting a thrombus or other blood particulate matter of a threshold size within a vessel, comprising:
   a filter having a head and a plurality of legs extending distally therefrom, configured to capture the thrombus or other blood particulate matter of at least a threshold size;
   at least one impedance element positioned distal to the head and configured to detect a presence of the thrombus or other blood particulate matter of at least a threshold size within the filter by obtaining data within a bloodstream when the filter is positioned within the bloodstream; and
   a sheath having a distal balloon positioned thereon, the sheath configured to be positioned around at least part of the filter within a blood vessel, wherein the balloon is configured for inflation within the blood vessel, wherein the inflation causes the balloon to inflate both outwardly toward a blood vessel wall, and proximally along the sheath and wherein the balloon at least partially surrounds the filter when inflated.

2. The device of claim 1, wherein the at least one impedance element comprises an excitation electrode configured to generate an electric field within the bloodstream when the filter is positioned within the bloodstream of a vessel.

3. The device of claim 1, wherein the at least one impedance element comprises a detection electrode configured to detect conductance data within the bloodstream when the filter is positioned within the bloodstream of a vessel.

4. The device of claim 1, wherein the at least one impedance element comprises a combination excitation and detection electrode configured to both excite an electric field and detect conductance data within the electric field in the bloodstream when the filter is positioned within the bloodstream of a vessel.

5. The device of claim 1, wherein the device further comprises at least one pressure sensor configured to obtain pressure data within a bloodstream, and wherein the pressure data indicates presence of the thrombus or other blood particulate matter of at least a threshold size within the filter.

6. The device of claim 1, wherein the device further comprises at least one fiber-optic sensor configured to obtain light data within a bloodstream, and wherein the light data indicates presence of the thrombus or other blood particulate matter of at least a threshold size within the filter.

7. The device of claim 1, wherein the device is at least partially coated with a coating comprising one or more fibroblast growth factor inhibitors.

8. The device of claim 1, wherein the legs form a generally conical configuration and further comprise barbs on the distal ends thereof, the barbs configured for detachable engagement with vessel walls to hold the filter in place within the bloodstream of the vessel.

9. A system for detecting a thrombus or other blood particulate matter of a threshold size within a vessel, comprising:
   a device, comprising:
      a filter having a head and a plurality of legs extending distally therefrom, configured to capture the thrombus or other blood particulate matter of at least a threshold size; and
      at least one impedance element positioned distal to the head and configured to detect a presence of the thrombus or other blood particulate matter of at least a threshold size within the filter by obtaining data within a bloodstream when the filter is positioned within the bloodstream; and
   a console operably coupled to the device, configured to wirelessly obtain data from the device, based the data received from the at least one impedance element positioned within the bloodstream of a vessel;
   wherein the system further comprises a sheath having a distal balloon positioned thereon, the sheath configured to be positioned around at least part of the filter within a blood vessel, wherein the balloon is configured for inflation within the blood vessel, wherein the inflation causes the balloon to inflate both outward toward the blood vessel, and proximally along the sheath, and wherein the balloon at least partially surrounds the blood filter device when inflated.

10. The system of claim 9, wherein the device may further comprise a filter transmitter/receiver, and wherein the console may further comprise a console transmitter/receiver, the filter transmitter/receiver operably coupled to the console transmitter/receiver to both transmit and receive the data detected by the at least one impedance element to and from the console.

11. The system of claim 10, wherein the filter transmitter/receiver and the console transmitter/receiver are operably coupled via a bidirectional radio frequency link.

12. The system of claim 9, further comprising a display operably coupled to the console, the display configured to visually or audibly provide the data received from the at least one impedance element positioned within the bloodstream of a vessel.

13. The system of claim 9, further comprising a remote computer operably coupled to the console, wherein the remote computer, the console, and the device can communicate with one another through a wireless network.

14. The system of claim 9, wherein the device is at least partially coated with a coating comprising a fibroblast growth factor inhibitor.

15. The system of claim 9, wherein the at least one impedance element comprises a combination excitation and detection electrode configured to both excite an electric field and detect conductance data within the electric field in the bloodstream when the filter is positioned within the bloodstream of a vessel.

16. The system of claim 9, wherein the device further comprises at least one sensor configured to obtain data within a bloodstream, and wherein the sensor data indicates presence of the thrombus or other blood particulate matter of at least a threshold size within the filter.

17. A method for safely removing a blood filter device from within a blood vessel, comprising the steps of:

surrounding at least part of the blood filter device with a sheath retrieval device, the blood filter device configured to capture a thrombus or other blood particulate matter of at least a threshold size, the blood filter device comprising:
    a head and a plurality of legs extending therefrom, and
    at least one impedance element positioned distal to the head and configured to detect a presence of the thrombus or other blood particulate matter of at least a threshold size within the blood filter device by obtaining data within a bloodstream when the blood filter device is positioned within the bloodstream; and inflating a balloon positioned on a distal end of the sheath retrieval device, wherein inflating the balloon within the blood vessel causes the balloon to inflate both outwardly toward blood vessel walls, and proximally along the sheath, wherein the balloon at least partially surrounds the blood filter device when inflated; and retracting the blood filter device up into the sheath retrieval device while the balloon provides continuous pressure against the blood vessel walls to safely detach the legs of the blood filter device from the blood vessel walls of a patient.

18. The method of claim 17, wherein surrounding at least part of the blood filter device further comprises inserting a catheter having a sheath retrieval device into the blood vessel of the patient.

* * * * *